US011686484B2

(12) United States Patent
Hilton

(10) Patent No.: US 11,686,484 B2
(45) Date of Patent: Jun. 27, 2023

(54) VIRUS ELIMINATION ASSEMBLY

(71) Applicant: Oswald Hilton, Spanaway, WA (US)

(72) Inventor: Oswald Hilton, Spanaway, WA (US)

(*) Notice: Subject to any disclaimer, the term of this patent is extended or adjusted under 35 U.S.C. 154(b) by 48 days.

(21) Appl. No.: 17/388,580

(22) Filed: Jul. 29, 2021

(65) Prior Publication Data

US 2023/0030935 A1 Feb. 2, 2023

(51) Int. Cl.
| F24F 8/22 | (2021.01) |
| B01D 46/00 | (2022.01) |
| A61L 9/20 | (2006.01) |
| F24F 8/80 | (2021.01) |
| F24F 8/10 | (2021.01) |

(52) U.S. Cl.
CPC ............. *F24F 8/22* (2021.01); *A61L 9/20* (2013.01); *B01D 46/0005* (2013.01); *B01D 46/0006* (2013.01); *B01D 46/0013* (2013.01); *B01D 46/0028* (2013.01); *F24F 8/10* (2021.01); *F24F 8/80* (2021.01); *A61L 2209/14* (2013.01)

(58) Field of Classification Search
CPC .............. B01D 46/00; B01D 46/0005; B01D 46/0006; B01D 46/0013; B01D 46/0028
See application file for complete search history.

(56) References Cited

U.S. PATENT DOCUMENTS

| D304,854 S | 11/1989 | Stackhouse |
| 5,616,172 A | 4/1997 | Tuckerman |
| 6,053,968 A | 4/2000 | Miller |
| 6,503,458 B1 | 1/2003 | Ogle |
| 6,680,028 B1 | 1/2004 | Harris |
| 10,471,170 B2 | 11/2019 | Lee |
| 2008/0101998 A1 | 5/2008 | Armstrong |
| 2020/0075972 A1 | 3/2020 | Jorgenson |

FOREIGN PATENT DOCUMENTS

| CN | 208170585 U | * 11/2018 |
| CN | 211892784 U | * 11/2020 |
| WO | WO2020047075 | 3/2020 |

* cited by examiner

*Primary Examiner* — Robert A Hopkins

(57) ABSTRACT

A virus elimination assembly for sterilizing air includes a base that is hollow. An intake vent is pivotally coupled to the base to direct air into the base. A canister is coupled to the base and the canister is in fluid communication with an interior of the base. A filter tray is slidably positioned in the canister and a filter is integrated to pass air therethrough. A blower tray is slidably positioned in the canister and a blower is integrated therein to blow air when the blower is turned on. A light tray is slidably positioned in the canister and a light emitter is integrated therein to eliminate viruses and bacteria. An exhaust vent is pivotally integrated into the canister to direct the air that has been sanitized by the light emitter out of the exhaust vent.

10 Claims, 5 Drawing Sheets

VIRUS ELIMINATION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to virus elimination device and more particularly pertains to a new virus elimination device for sterilizing air in a desired location. The device includes a canister with a plurality of trays that are slidably integrated into the canister. A filter, a blower and a light emitter are each integrated into a respective tray. The filter filters the air, the blower blows the air and the light emitter sterilizes the air.

(2) Description of Related Art Including Information Disclosed Under 37 CFR 1.97 and 1.98

The prior art relates to virus elimination devices including a variety of air purifiers that include a blower and an ultraviolet light. The prior art also discloses a variety of air purifiers that include a filter and a blower. In no instance does the prior art disclose an air purifier that has a filter, a blower and a light emitter that are each integrated into a respective tray in a canister.

BRIEF SUMMARY OF THE INVENTION

An embodiment of the disclosure meets the needs presented above by generally comprising a base is hollow. An intake vent is pivotally coupled to the base to direct air into the base. A canister is coupled to the base and the canister is in fluid communication with an interior of the base. A filter tray is slidably positioned in the canister and a filter is integrated to pass air therethrough. A blower tray is slidably positioned in the canister and a blower is integrated therein to blow air when the blower is turned on. A light tray is slidably positioned in the canister and a light emitter is integrated therein to eliminate viruses and bacteria. An exhaust vent is pivotally integrated into the canister to direct the air that has been sanitized by the light emitter out of the exhaust vent.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
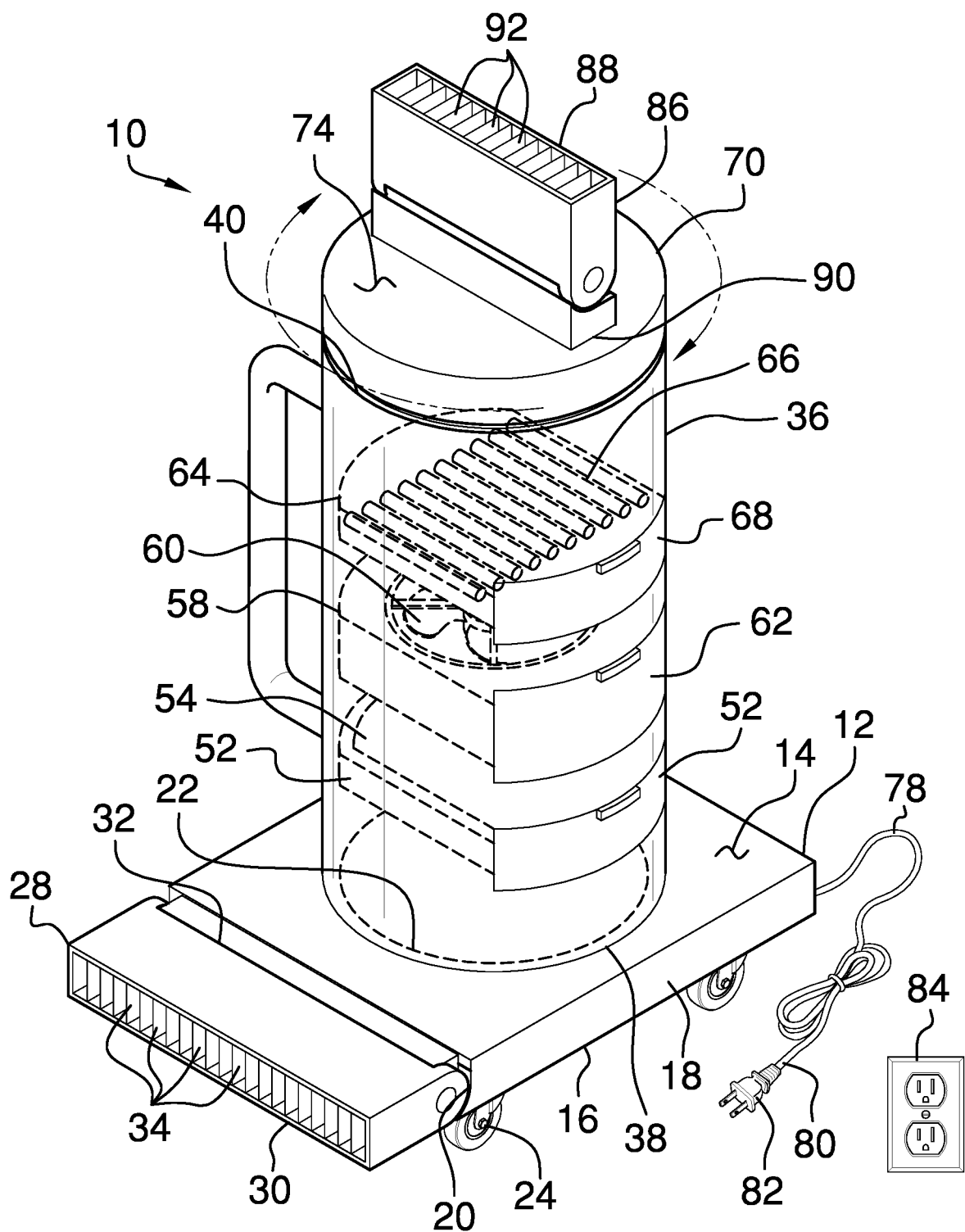
FIG. 1 is a perspective view of a virus elimination assembly according to an embodiment of the disclosure.
Figure 2:
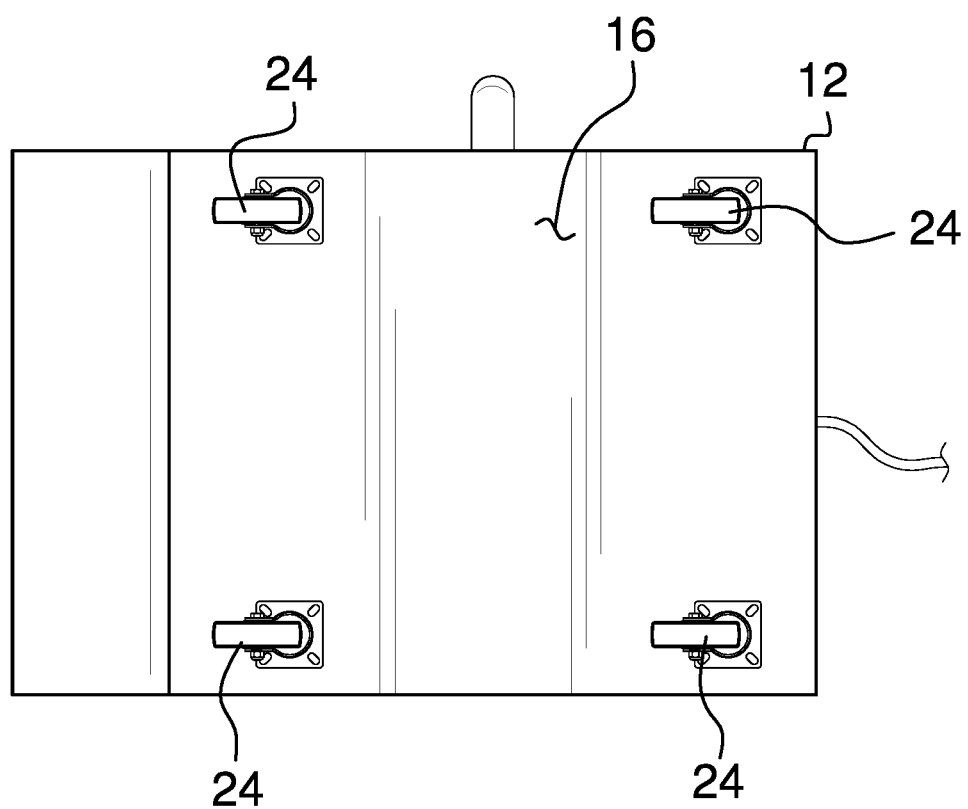
FIG. 2 is a bottom view of an embodiment of the disclosure.
Figure 3:
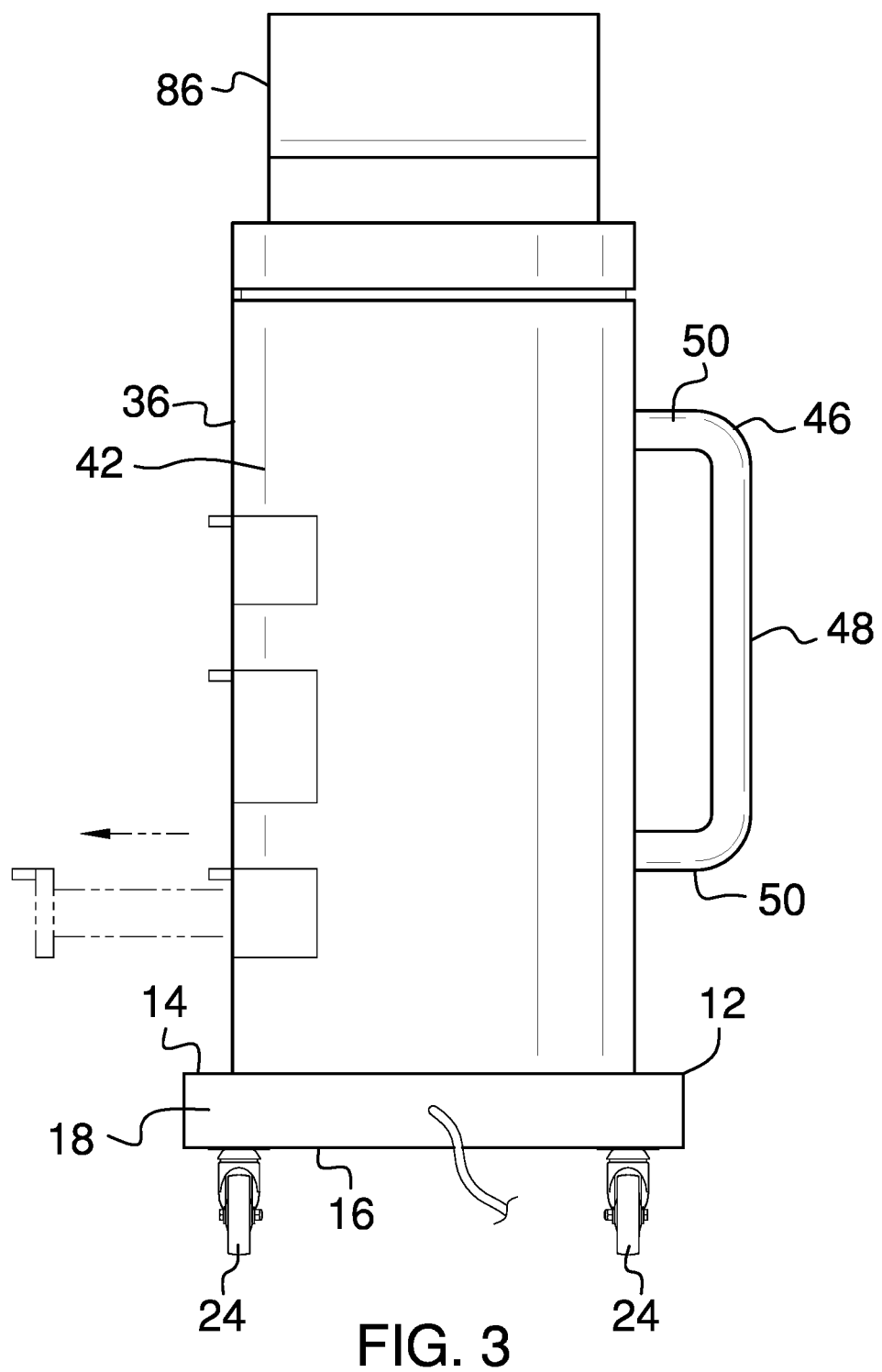
FIG. 3 is a back view of an embodiment of the disclosure.
Figure 4:
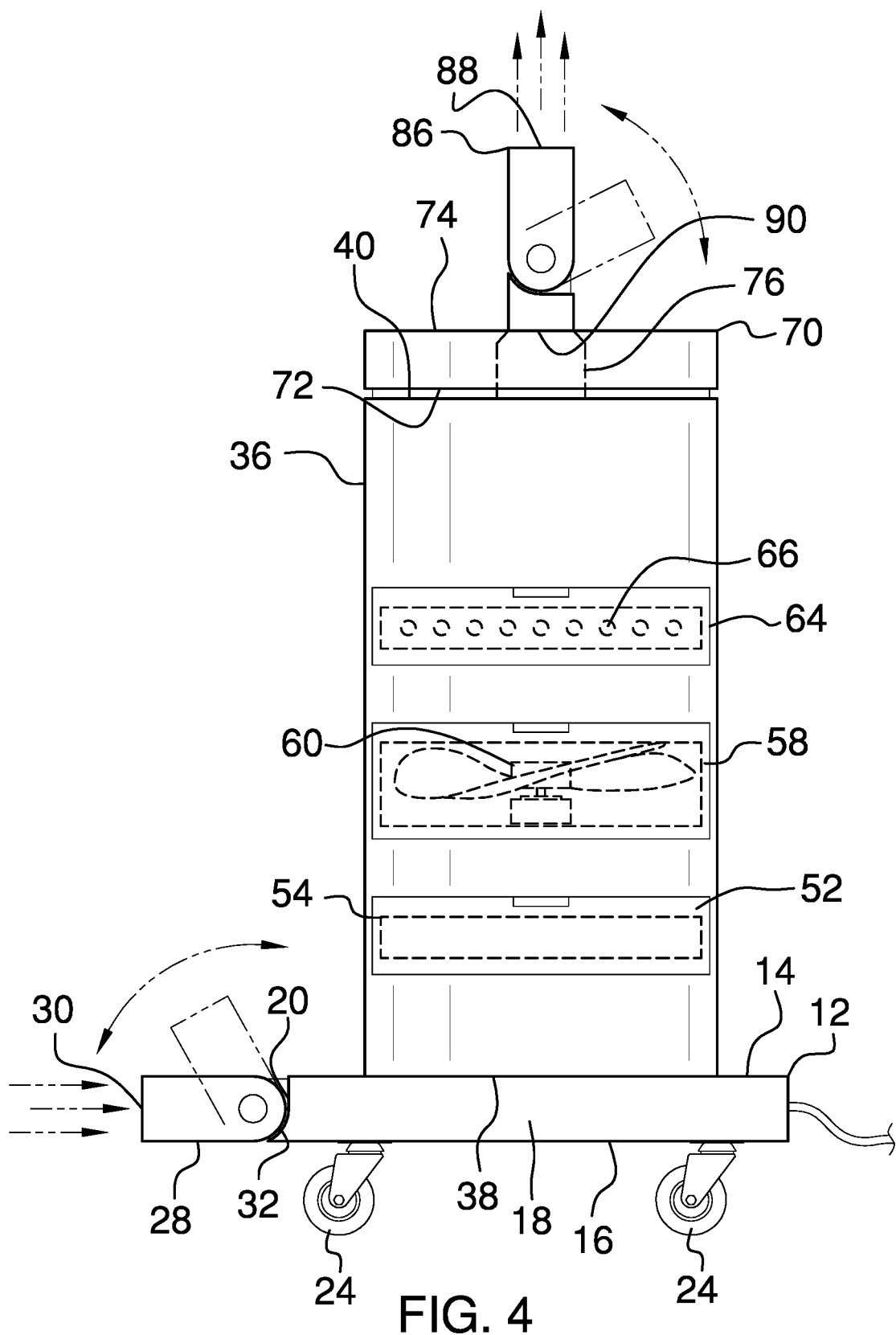
FIG. 4 is a left side view of an embodiment of the disclosure.
Figure 5:
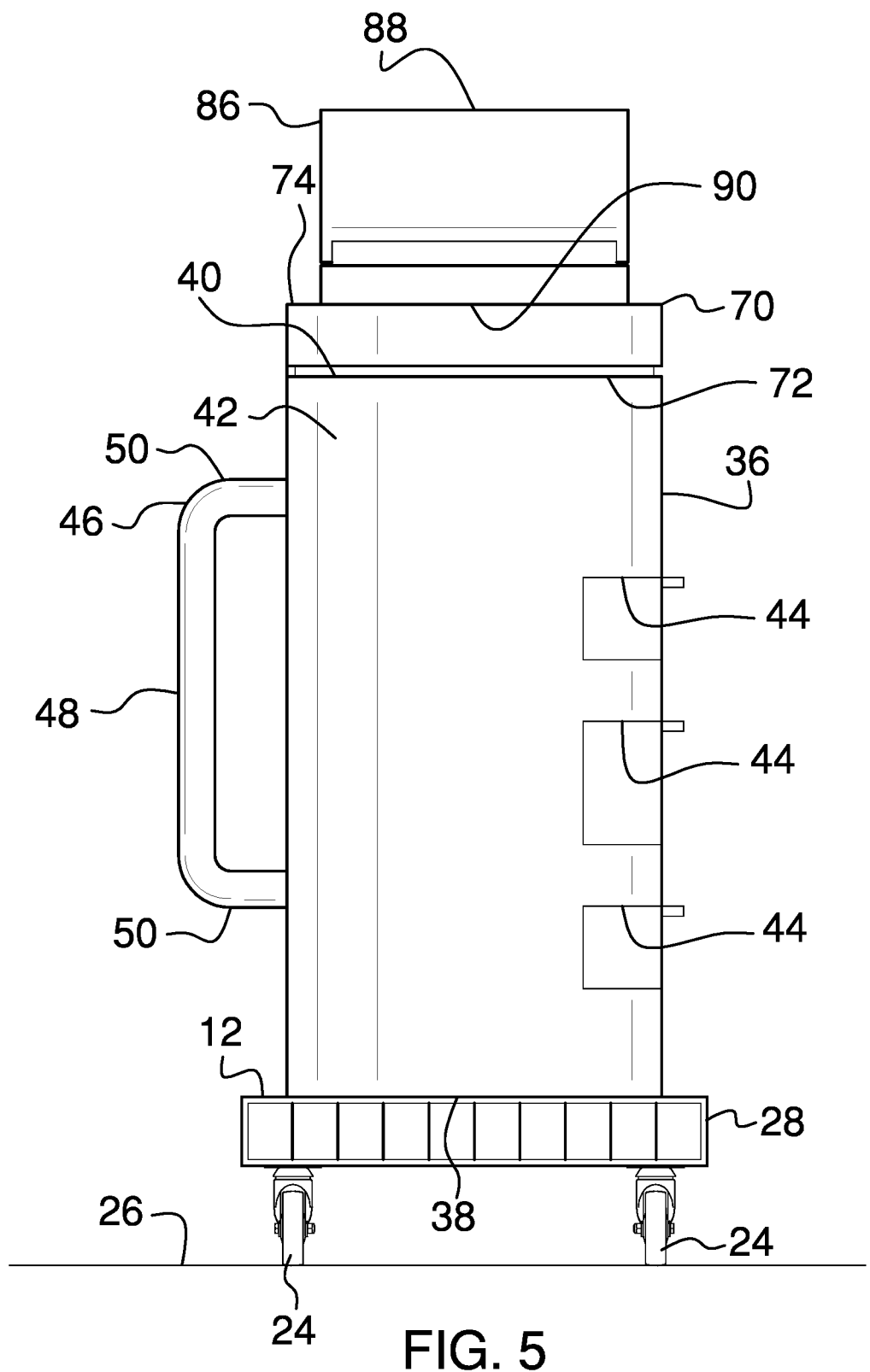
FIG. 5 is a front view of an embodiment of the disclosure.

With reference now to the drawings, and in particular to FIGS. 1 through 5 thereof, a new virus elimination device embodying the principles and concepts of an embodiment of the disclosure and generally designated by the reference numeral 10 will be described.

As best illustrated in FIGS. 1 through 5, the virus elimination assembly 10 generally comprises a base 12 that is hollow and which has a top surface 14, a bottom surface 16 and a perimeter edge 18 extending between the top surface 14 and the bottom surface 16. The perimeter edge 18 has a front side 20, the front side 20 is open into an interior of the base 12 and the top surface 14 has an opening 22 extending into the interior of the base 12. A plurality of the rollers 24 is each rotatably coupled to the base 12 to roll along a support surface 26. Each of the rollers 24 is positioned on the bottom surface 16 of the base 12 to support the base 12 above the support surface 26.

An intake vent 28 is pivotally coupled to the base 12 such that the intake vent 28 is in fluid communication with the interior of the base 12 to direct air into the base 12. The intake vent 28 has a front end 30 and a back end 32, and the back end 32 is pivotally coupled to the front side 20 of the perimeter edge 18 of the base 12. In this way the front end 30 of the intake vent 28 can be directed at a variety of angles with respect to the front side 20 of the perimeter edge 18 of the base 12. The intake vent 28 may have a plurality of vanes 34 inside the intake vent 28 that extend between the front end 30 and the back end 32.

A canister 36 is provided and the canister 36 is coupled to the base 12. The canister 36 is hollow and the canister 36 is in fluid communication with an interior of the base 12. The canister 36 has a lower end 38, an upper end 40 and an outer wall 42 extending therebetween. The lower end 38 is open and the lower end 38 is coupled to the top surface 14 of the base 12 having the lower end 38 being aligned with the opening in the top surface 14. In this way the canister 36 receives air from the base 12. The outer wall 42 has a plurality of tray openings 44 each extending into an interior of the canister 36. The tray openings 44 are spaced apart from each other and are distributed between the lower end 38 and the upper end 40. Additionally, each of the tray openings 44 is elongated to extend substantially around a circumference of the canister 36. The canister 36 may have a height ranging between approximately 3.0 feet and 4.0 feet, and a diameter ranging between approximately 15.0 inches and 20.0 inches.

A handle 46 is coupled to the canister 36 such that the handle 46 can be gripped for rolling the canister 36 into a preferred location. The handle 46 has a central member 48 extending between a pair of outward members 50, and each of the outward members 50 is oriented perpendicular to the central member 48. Each of the outward members 50 extends laterally away from the outer wall 42 of the canister 36 having the central member 48 being vertically oriented such that the central member 48 can be gripped.

A filter tray 52 is slidably positioned in the canister 36 and a filter 54 is integrated into the filter tray 52. The filter 54 is comprised of an air permeable material to pass air therethrough while removing particles from the air. The filter 54 may be a high efficiency particulate air (HEPA) filter 54 or other type of filter 54 that is capable of capturing particles of 0.01 micron or larger in size. The filter tray 52 is slidably positioned in a respective one of the tray openings 44 having the filter tray 52 lying on a horizontal plane. The filter tray 52 has a front panel 56 and the front panel 56 is concavely arcuate such that the front panel 56 conforms to curvature of the outer wall 42 of the canister 36 when the filter tray 52 is closed.

A blower tray 58 is slidably positioned in the canister 36 and a blower 60 is integrated into the blower tray 58 to blow air when the blower 60 is turned on. The blower tray 58 is insertable into a respective one of the tray openings 44 such that the blower tray 58 is positioned above the filter tray 52 and the blower tray 58 lies on a horizontal plane when the blower tray 58 is inserted into the respective tray opening 44. In this way the blower 60 urges air inwardly through the intake vent 28 having the air passing upwardly through the filter 54 and upwardly toward the upper end 40 of the canister 36 when the blower 60 is turned on. The blower tray 58 has a front panel 62 and the front panel 62 of the blower tray 58 is concavely arcuate such that the front panel 62 of the blower tray 58 conforms to the curvature of the outer wall 42 of the canister 36 when the blower tray 58 is closed. Additionally, the blower 60 may include an electric motor and a fan that is rotated by the electric motor.

A light tray 64 is slidably positioned in the canister 36 and a light emitter 66 is integrated into the light tray 64 to emit light into the canister 36 when the light emitter 66 is turned on. The light emitter 66 has an operational frequency in the ultraviolet spectrum of light to eliminate viruses and bacteria, and the light emitter 66 may comprise a light emitting diode or other type of electronic light emitter. The light tray 64 is insertable into a respective one of the tray openings 44 having the light tray 64 being positioned above the blower 60. In this way the light emitter 66 kills viruses and bacteria in the air that is blown by the blower 60. The light tray 64 lies on a horizontal plane when the light tray 64 is inserted into the respective tray opening 44. Additionally, the light tray 64 has a front panel 68 and the front panel 68 of the light tray 64 is concavely arcuate such that the front panel 68 of the light tray 64 conforms to the curvature of the outer wall 42 of the canister 36.

A disk 70 is provided and the disk 70 is rotatably integrated into the canister 36. The disk 70 has a bottom surface 72 and a top surface 74, and the bottom surface 72 rotatably engages the upper end 40 of the canister 36. The disk 70 has an air passage 76 extending through the top surface 74 and the bottom surface 72 to pass air through the disk 70. A power cord 78 is coupled to and extends away from the base 12, and the power cord 78 is electrically coupled to the blower 60 and the light emitter 66. The power cord 78 has a distal end 80 with respect to the base 12, a male plug 82 is electrically coupled to the distal end 80 and the male plug 82 can be plugged into a female electrical outlet 84.

An exhaust vent 86 is pivotally integrated into the disk 70 such that the exhaust vent 86 is in fluid communication with the interior of the canister 36. In this way the exhaust vent 86 can direct the air that has been sanitized by the light emitter 66 out of the exhaust vent 86. The exhaust vent 86 has a top end 88 and a bottom end 90, and the bottom end 90 is pivotally coupled to the top surface 74 of the disk 70 having the bottom end 90 being aligned with the air passage 76 in the disk 70. Moreover, the exhaust vent 86 can be positioned at a variety of angles with respect to the top surface 74 of the disk 70 to direct the air in a variety of directions. The exhaust vent 86 may include a plurality of vanes 92 that extend between the top end 88 and the bottom end 90 of the exhaust vent 86.

In use, the base 12 is rolled to a desired location and the power cord 78 is plugged into the power source. Thus, the blower 60 is turned on and the light emitter 66 is turned on. In this way air is urged inwardly through the intake vent 28, filtered through the filter 54, sanitized by the light emitter 66 and ultimately urged outwardly through the exhaust vent 86. In this way the air in the desired location can be sterilized to reduce the risk of airborne transmission of infectious diseases. The desired location might be an examination room in a medical facility or other location where sterility is a high priority. The filter 54 can be replaced by opening the filter tray 52, the blower 60 can be serviced by opening the blower tray 58 and the light emitter 66 can be serviced by opening the light tray 64.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. A virus elimination assembly for eliminating airborne viruses in a pre-determined area, said assembly comprising:

a base being hollow;

a plurality of rollers, each of said rollers being rotatably coupled to said base wherein each of said rollers is configured to roll along a support surface;

an intake vent being pivotally coupled to said base such that said intake vent is in fluid communication with an interior of said base wherein said intake vent is configured to direct air into said base;

a canister being coupled to said base, said canister being hollow, said canister being in fluid communication with said interior of said base;

a handle being coupled to said canister wherein said handle is configured to be gripped for rolling said canister into a preferred location;

a filter tray being slidably positioned in said canister, said filter tray having a filter being integrated therein, said filter being comprised of an air permeable material wherein said filter is configured to pass air therethrough;

a blower tray being slidably positioned in said canister, said blower tray having a blower being integrated therein wherein said blower is configured to blow air when said blower is turned on;

a light tray being slidably positioned in said canister, said light tray having a light emitter being integrated therein wherein said light emitter is configured to emit light into said canister when said light emitter is turned on, said light emitter having an operational frequency in the ultraviolet spectrum of light wherein said light emitter is configured to eliminate viruses and bacteria;

a disk being rotatably integrated into said canister; and an exhaust vent being pivotally integrated into said disk such that said exhaust vent is in fluid communication with said interior of said canister wherein said exhaust vent is configured to direct the air that has been sanitized by said light emitter out of said exhaust vent.

2. The assembly according to claim 1, wherein:

said base has a top surface, a bottom surface, and a perimeter edge extending between said top surface and said bottom surface, said perimeter edge having a front side, said front side being open into said interior of said base, said top surface having an opening extending into said interior of said base; and said intake vent has a front end and a back end, said back end being pivotally coupled to said front side of said perimeter edge of said base thereby facilitating said front end of said intake vent to be directed at a variety of angles with respect to said front side of said perimeter edge of said base.

3. The assembly according to claim 2, wherein said canister has a lower end, an upper end and an outer wall extending therebetween, said lower end being open, said lower end being coupled to said top surface of said base having said lower end being aligned with said opening in said top surface wherein said canister is configured to receive air from said base, said outer wall having a plurality of tray openings each extending into said interior of said canister, said tray openings being spaced apart from each other and being distributed between said lower end and said upper end, each of said tray openings being elongated to extend substantially around a circumference of said canister.

4. The assembly according to claim 3, wherein said handle has a central member extending between a pair of outward members, each of said outward members being oriented perpendicular to said central member, each of said outward members extending laterally away from said outer wall of said canister having said central member being vertically oriented wherein said central member is configured to be gripped.

5. The assembly according to claim 3, wherein said filter tray is slidably positioned in said a respective one of said tray openings having said filter tray lying on a horizontal plane, said filter tray having a front panel, said front panel being concavely arcuate such that said front panel conforms to curvature of said outer wall of said canister when said filter tray is closed.

6. The assembly according to claim 3, wherein said blower tray is insertable into a respective one of said tray openings such that said blower tray is positioned above said filter tray wherein said blower is configured to urge air inwardly through said intake vent having the air passing upwardly through said filter and upwardly toward said upper end of said canister when said blower is turned on, said blower tray lying on a horizontal plane when said blower tray is inserted into said respective tray opening, said blower tray having a front panel, said front panel of said blower tray being concavely arcuate such that said front panel of said blower tray conforms to said curvature of said outer wall of said canister when said blower tray is closed.

7. The assembly according to claim 3, wherein said light tray is insertable into a respective one of said tray openings having said light tray being positioned above said blower wherein said light emitter is configured to kill viruses and bacteria in the air being blown by said blower, said light tray lying on a horizontal plane when said light tray is inserted into said respective tray opening, said light tray having a front panel, said front panel of said light tray being concavely arcuate such that said front panel of said light tray conforms to said curvature of said outer wall of said canister.

8. The assembly according to claim 3, wherein said disk has a bottom surface and a top surface, said bottom surface rotatably engaging said top end of said canister, said disk having an air passage extending through said top surface and said bottom surface wherein said air passage is configured to pass air through said disk.

9. The assembly according to claim 8, wherein said exhaust vent has a top end and a bottom end, said bottom end being pivotally coupled to said top surface of said disk having said bottom end being aligned with said air passage.

10. A virus elimination assembly for eliminating airborne viruses in a pre-determined area, said assembly comprising:

a base being hollow, said base having a top surface, a bottom surface, and a perimeter edge extending between said top surface and said bottom surface, said perimeter edge having a front side, said front side being open into an interior of said base, said top surface having an opening extending into said interior of said base;

a plurality of rollers, each of said rollers being rotatably coupled to said base wherein each of said rollers is configured to roll along a support surface, each of said rollers being positioned on said bottom surface of said base wherein said rollers are configured to support said base above the support surface;

an intake vent being pivotally coupled to said base such that said intake vent is in fluid communication with said interior of said base wherein said intake vent is configured to direct air into said base, said intake vent having a front end and a back end, said back end being pivotally coupled to said front side of said perimeter edge of said base thereby facilitating said front end of said intake vent to be directed at a variety of angles with respect to said front side of said perimeter edge of said base;

a canister being coupled to said base, said canister being hollow, said canister being in fluid communication with said interior of said base, said canister having a lower end, an upper end and an outer wall extending therebetween, said lower end being open, said lower end being coupled to said top surface of said base having said lower end being aligned with said opening in said top surface wherein said canister is configured to receive air from said base, said outer wall having a plurality of tray openings each extending into an interior of said canister, said tray openings being spaced apart from each other and being distributed between said tower end and said upper end, each of said tray openings being elongated to extend substantially around a circumference of said canister;

a handle being coupled to said canister wherein said handle is configured to be gripped for rolling said canister into a preferred location, said handle having a central member extending between a pair of outward members, each of said outward members being oriented perpendicular to said central member, each of said outward members extending laterally away from said outer wall of said canister having said central member being vertically oriented wherein said central member is configured to be gripped;

a filter tray being slidably positioned in said canister, said filter tray having a filter being integrated therein, said fitter being comprised of an air permeable material wherein said filter is configured to pass air therethrough, said filter tray being slidably positioned in said a respective one of said tray openings having said filter tray lying on a horizontal plane, said filter tray having a front panel, said front panel being concavely arcuate such that said front panel conforms to curvature of said outer watt of said canister when said filter tray is closed;

a blower tray being slidably positioned in said canister, said blower tray having a blower being integrated therein wherein said blower is configured to blow air when said blower is turned on, said blower tray being insertable into a respective one of said tray openings such that said blower tray is positioned above said filter tray wherein said blower is configured to urge air inwardly through said intake vent having the air passing upwardly through said filter and upwardly toward said upper end of said canister when said blower is turned on, said blower tray lying on a horizontal plane when said blower tray is inserted into said respective tray opening, said blower tray having a front panel, said front panel of said blower tray being concavely arcuate such that said front panel of said blower tray conforms to said curvature of said outer wall of said canister when said blower tray is closed;

a light tray being slidably positioned in said canister, said light tray having a light emitter being integrated therein wherein said light emitter is configured to emit light into said canister when said light emitter is turned on, said light emitter having an operational frequency in the ultraviolet spectrum of light wherein said light emitter is configured to eliminate viruses and bacteria, said light tray being insertable into a respective one of said tray openings having said light tray being positioned above said blower wherein said light emitter is configured to kill viruses and bacteria in the air being blown by said blower, said light tray lying on a horizontal plane when said light tray is inserted into said respective tray opening, said light tray having a front panel, said front panel of said light tray being concavely arcuate such that said front panel of said light tray conforms to said curvature of said outer wall of said canister;

a disk being rotatably integrated into said canister, said disk having a bottom surface and a top surface, said bottom surface rotatably engaging said top end of said canister, said disk having an air passage extending through said top surface and said bottom surface wherein said air passage is configured to pass air through said disk;

an exhaust vent being pivotally integrated into said disk such that said exhaust vent is in fluid communication with said interior of said canister wherein said exhaust vent is configured to direct the air that has been sanitized by said light emitter out of said exhaust vent, said exhaust vent having a top end and a bottom end, said bottom end being pivotally coupled to said top surface of said disk having said bottom end being aligned with said air passage; and a power cord being coupled to and extending away from said base, said power cord being electrically coupled to said blower and said light emitter, said power cord having a distal end with respect to said base, said distal end having a male plug being electrically coupled thereto wherein said male plug is configured to be plugged into a female electrical outlet.

* * * * *